United States Patent [19]

Hartmann et al.

[11] Patent Number: 4,839,370

[45] Date of Patent: Jun. 13, 1989

[54] NOVEL DERIVATIVES OF 3-ARYL-3-CYCLOALKYL-PIPERIDINE-2,6-DIONE

[75] Inventors: Rolf W. Hartmann, Bad Abbach; Christine Batzl, Schwandorf, both of Fed. Rep. of Germany

[73] Assignee: Asta-Pharma AG, Bielefeld, Fed. Rep. of Germany

[21] Appl. No.: 79,964

[22] Filed: Jul. 31, 1987

[30] Foreign Application Priority Data

Jul. 31, 1986 [DE] Fed. Rep. of Germany ........ 3625415

[51] Int. Cl.$^4$ .................... A61K 31/45; C07D 211/88
[52] U.S. Cl. .................................... 514/328; 546/219
[58] Field of Search ........................ 546/219; 514/328

[56] References Cited

U.S. PATENT DOCUMENTS 2,848,455  8/1958  Hoffmann et al. ................... 546/219
3,057,867 10/1962  Taub ..................................... 546/219

FOREIGN PATENT DOCUMENTS 570974   2/1959  Canada ................................ 546/219
1445652  1/1969  Fed. Rep. of Germany ...... 546/219
720198  12/1954  United Kingdom ................ 546/219

OTHER PUBLICATIONS

Allan B. Foster et al, J. Med. Chem. (1983), vol. 26, pp. 50–54.
Allan B. Foster et al, J. Med. Chem. (1985), vol. 28, pp. 200–204.
Rolf W. Hartmann et al, J. Med. Chem. (1986), vol. 29, pp. 1362–1369.

*Primary Examiner*—Glennon H. Hollrah
*Assistant Examiner*—Susan P. Treanor
*Attorney, Agent, or Firm*—Cushman, Darby & Cushman

[57] ABSTRACT

Novel 3-aryl-3-cycloalkyl-piperidine-2,6-dione derivatives of the general formula I:

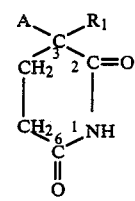

in which A is a 4-aminophenyl radical or a pyridyl-(4)-radical and $R_1$ is a saturated or unsaturated $C_3$–$C_{10}$-cycloalkyl radical or a $C_3$–$C_{12}$-alkenyl radical as well as physiologically acceptable salts thereof. The compounds are useful as inhibitors of estrogen biosynthesis. The compounds are made by a process which includes the step of heating a compound of the formula II

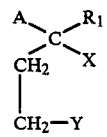

wherein A and $R_1$ have the meanings given above, and in addition A may also be a phenyl radical or a 4-nitrophenyl radical, X and Y are the same or different and repesent CN or $COOC_1$–$C_6$-alkyl and X or Y may also be COOH or a carboxylic acid ester group of the formula $COOC_1$–$C_6$-alkyl group, in a high boiling solvent at a temperature between 50° and 200° C. in particular between 80° and 100° C., optionally in the presence of condensation agents to form a piperidine dione ring.

7 Claims, No Drawings

NOVEL DERIVATIVES OF 3-ARYL-3-CYCLOALKYL-PIPERIDINE-2,6-DIONE

The present invention relates to novel derivatives of 3aryl-3-cycloalkyl-piperidine-2,6-dione which are useful as inhibitors of estrogen biosynthesis and for the treatment of medical conditions which are affected by the presence of estrogens.

BACKGROUND OF THE INVENTION

Inhibitors of estrogen biosynthesis constitute a new therapeutic concept for the treatment of estrogen dependent diseases, in particular estrogen dependent tumors such as breast cancer. By means of the inhibition of aromatase, which is the enzyme which catalyses the last synthetic step, a selective inhibition of estrogen biosynthesis is possible. Aminoglutethimide (3-[4-aminophenyl]-3-ethyl-piperidine-2,6-dione) has been the only non-steroidal aromatase inhibitor which had been used therapeutically.

SUMMARY OF THE INVENTION

It is an object of the present invention to provide improved aromatase inhibitors for the treatment of estrogen dependent diseases, in particular for the treatment of hormone dependent tumors.

The compounds of the present invention possess the same or similar activity as the known compound aminoglutethimide and are useful for the same purposes as the known compound. However, in contradistinction thereto, they are active in considerably lower dosages, so that, for example, disturbing side effects such as desmolase inhibition do not appear or appear only to a small extent. In addition, undesired sedative activity does not occur when using the compounds according to the present invention.

Therefore, the compounds according to the present invention are, for example, suitable for the treatment of the following medical conditions in humans and in animals: estrogen dependent tumors, such as breast cancer, endometrial carcinoma, and also other estrogen dependent diseases such as endometriosis, gynaecomastia and idiopathic oligospermia. They may also be used as potential ovulation inhibitors and birth inducing agents and are suitable for the treatment and prevention of benign prostate hyperplasia.

The compounds of the present invention are 3-aryl-3cycloalkyl-piperidine-2,6-dione derivatives of the general Formula I:

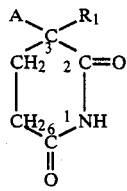

in which A is a 4-aminophenyl radical or a pyridyl-(4)-radical and $R_1$ is a saturated or unsaturated $C_3$–$C_{10}$-cycloalkyl radical or a $C_3$–$C_{12}$-alkenyl radical as well as physiologically acceptable salts thereof.

$C_3$–$C_{10}$-cycloalkyl radicals which may be used include in particular $C_4$–$C_8$-cycloalkyl radicals, for example cyclobutyl, cyclopentyl, cyclohexyl, cycloheptyl and cyclooctyl radicals.

If the $C_3$–$C_{10}$-cycloalkyl radical is unsaturated, it preferably contains one double bond and in this case the ring may especially contain from 5–10 ring members, preferably from 6–8 ring members.

Preferred $C_3$–$C_{12}$-alkenyl radicals, which may be straight-chain or branched, are in particular $C_3$–$C_8$ alkenyl radicals, preferably $C_3$–$C_6$-alkenyl radicals.

Particularly preferred compounds of Formula I are those wherein A is a 4-aminophenyl radical and $R_1$ is a $C_3$–$C_{10}$-cycloalkyl radical.

The compounds of the present invention contain one and possibly two or three asymmetric carbon atoms. Therefore, during their synthesis, it is possible for mixtures of diastereoisomers to be prepared. These mixtures may be separated in a conventional manner, for example by recrystallization. Racemates may be separated into the pure enantiostereoisomers using optically active auxiliary substances (for example optically active acids) in a manner kown per se. It is, however, also possible to use optically active or diastereomeric starting materials in the synthesis whereby the corresponding enantiosteriomeric or diastereomeric end products are produced. For practical use as pharmaceutical agents, one may employ pure isomers or mixtures of isomers.

Formula I comprises all possible enantiomers and diastereomers.

The present invention also provides a process for synthesis of compounds according to the Formula I which includes the step of heating a compound of the Formula II

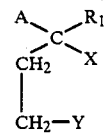

wherein A and $R_1$ have the meanings given above, and in addition A may also be a phenyl radical or a 4-nitrophenyl radical, X and Y are the same or different and represent CN or $COOC_1$–$C_6$-alkyl and X or Y may also be COOH. This compound is heated in a high boiling solvent at a temperature between 50° and 200° C., in particular between 80° and 100° C., optionally in the presence of condensation agents to form a piperidine dione ring. The process of the present invention may also include introducing a nitro group by nitration of a phenyl radical when A of compound II is a phenyl radical and then reducing the nitro radical to an amino group. If the group A of compound II is nitrophenyl, the process may include reducing the nitro group to an amino group. Reaction with acid may also convert the products obtained to their acid salts. Preferably, the compound is cyclized prior to nitration and/or reduction of the nitro group.

DETAILED DESCRIPTION OF PREFERRED EMBODIMENTS

Condensation agents which may be used in the process of the present invention include strong mineral acids ($H_2SO_4$, HCl, polyphosphoric acid) or strong bases ($NH_3$). In the case of the cyclization of diesters (i.e., when X and Y represent in each case the $COOC_1$–$C_6$-alkyl group) the use of $NH_3$ or urea is for example necessary.

Solvents which may be used for the cyclization include: lower aliphatic carboxylic acids having 1-6 carbon atoms such as formic acid, glacial acetic acid, propionic acid, anhydrides of lower aliphatic carboxylic acids having 2 to 4 C-atoms, such as acetic anhydride; basic solvents such as pyridine or lower alkyl amides of lower aliphatic carboxylic acids such as dimethyl formamide, diethyl acetamide, as well as mixtures of such agents. The reaction time may, for example, be from 2-10 hours.

If X and/or Y represent the ester group $COOC_1$-$C_6$-alkyl, then the alkyl group preferably contains from 1 to 4 carbon atoms, and more preferably it represents the ethoxycarboxyl group.

As mentioned above, when A represents a phenyl radical, a nitro group can be introduced therein by a conventional nitration reaction. Nitrating agents which can be used include, for example: nitric acid or mixtures of nitric acid with $H_2SO_4$, selenic acid or $BF_3$; mixtures of anhydrides or nitric acid (for example acetyl nitrate, benzoyl nitrate); nitronium compounds (halides, perchlorate, tetrafluoroborate); metal nitrates with and without the addition of acid; nitric acid esters with and without the addition of acids; nitroalkanes (for example tetranitromethane); nitrous acid or derivatives thereof (for example esters of nitrosonium hydrogen sulfate); nitrogen oxides.

The nitration may be carried out with or without additional solvents at temperatures between $-20$ and $+100°$ C. The reaction time is for example 1-80 hours. If solvents are used, then they may for example be: lower liquid aliphatic chlorohydrocarbons ($CHCl_3$, $CH_2Cl_2$, $CCl_4$); liquid alkanes (ligroin); lower aliphatic alcohols (ethanol); lower aliphatic or cycloaliphatic ethers (diethylether); lower aliphatic ketones (acetone); sulfonated hydrocarbons; nitromethane or acetonitrile.

Reduction of the nitro group may especially be carried out using catalytic hydrogenation. Catalysts which may be used include: Raney nickel, noble metals such am palladium and platinum as well as compounds thereof (e.g. oxides) with or without carriers (e.g. active charcoal, barium sulfate, calcium sulfate).

The hydrogenation of the nitro group is preferably carried out at a temperature between 20° and 120° C. and at a pressure from about 5-100 atmospheres in a solvent, for example, water, lower alcohols, lower aliphatic ethers, saturated cyclic ethers (e.g. dioxane, tetrahydrofuran), lower carboxylic acids having 1-4 carbon atoms (e.g. glacial acetic acid) or also liquid alkanes. In connection with the subsequent isolation of the reduced compounds, it may in many cases be advantageous when drying agents, such as anhydrous sodium or magnesium sulfate, are added to the mixture to be hydrogenated at the beginning of the reaction. The reduction can, however, also be carried out using nascent hydrogen, produced, for example, by zinc/hydrochloric acid, tin/hydrochloric acid, iron/hydrochloric acid or using salts of hydrogen sulfide, ammonium sulfide, sodium sulfide or sodium dithionite, at a temperature between about 20° and 100° C. or using activated aluminum in aqueous ether or with tin(II)-chloride/hydrochloric acid.

The novel starting materials of Formula II may be produced in the manner illustrated in Example 1.

The radical $R_1$ may be introduced by alkylation of the corresponding cyanide A-$CH_2$-CN or the corresponding ester A—$CH_2$—$COOC_1$—$C_6$-alkyl, at a temperature between 60° and 120° C. in an inert solvent (toluene, benzene), in the presence of basic compounds (alkali amides, alkali hydrides such as $NaNH_2$, NaH; alkali alcoholates such as potassium tert.-butylate; butyl lithium) using the corresponding halide (e.g. chloride, bromide, iodide), sulfates, sulfonates or tosylates. This alkylation may also be carried out using phase transfer conditions. The so-obtained compound A—CH($R_1$)—X (in which the meanings of X are as given above) is then for example reacted with a compound $CH_2$=CH-Y (wherein Y is CN, $COOC_1$—$C_6$-alkyl or $CO_2H$) at a temperature between 20 and 120° C. in the presence of bases (e.g. quaternary ammonium compounds such as Triton B, alkali alcoholates, alkali amides, alkali hydroxides such as KOH or NaOH). Anhydrous solvents which may be used in this connection include: cyclic ethers (e.g. dioxane, tetrahydrofuran), benzene, toluene, tert.-butyl alcohol and acetonitrile. The base may be used in an amount equivalent to the CH-acid component.

Where A represents a pyridyl-(4)-radical, the starting material A—CH($R_1$)—CN or A—CH($R_1$)—$COOC_1$—$C_6$-alkyl may also be obtained by the reaction of A-Cl with $R_1CH_2X$ (wherein X=CN or $COOC_1$—$C_6$-alkyl) at a temperature between 60 and 120° C. in an inert anhydrous solvent (e.g. benzene or toluene) in the presence of a base (e.g. alkali amides, alkali hydrides such as $NaNH_2$, NaH; alkali alcoholates such as potassium tert.-butylate). See in this connection also J. Am. Chem. Soc. 73, page 4925 (1951).

This form of the process of the invention may be carried out for example as follows: 2-cycloalkyl-2-(4-pyridyl)acetonitrile (2-alkenyl-. . . ; 2-cycloalkenyl-. . .) 0.1 mol of cycloalkyl acetonitrile (alkenyl-. . . or cycloalkenyl-. . .) and 0.1 mol $NaNH_2$ are heated for 2 hours at 80° C. in 50 ml toluene. After cooling, 0.1 mol of 4-chloropyridine are added dropwise to 15 ml of toluene and the mixture is heated for 1 hour under reflux. After cooling the reaction product is shaken with normal HCl (1N CHl).

After neutralization, the mixture is extracted with $CH_2Cl_2$ and dried over $Na_2SO_4$. The solvent is removed and the crude product is purified by chromatography.

Alternatively, the $BF_4$ salt of the N-triphenylmethyl-pyridinium cation according to J.C.S. Perkin, Transactions I 2476 (1981) is mixed with the compound $R_1CH_2X$ (wherein X =CN, $COOC_1$-$C_6$-alkyl or COOH) at temperatures between $-80°$ C. and $+120°$ C. in an inert solvent (e.g. toluene, benzene, cyclic ethers such as dioxane, tetrahydrofuran, liquid alkanes) in the presence of a base. Bases which may be used include, for example: alkali amides, alkali hydrides ($NaNH_2$, lithium diisopropylamide, lithium diisopropylcyclohexylamide, NaH), alkali alcoholates (potassium tert.-butylate).

This embodiment of the present invention may for example be carried out as follows: 2-cycloalkyl-2-(4-pyridyl)acetonitrile (2-alkenyl-. . . ; 2-cycloalkenyl. . .)

To a solution of 0.1 mol of lithium diisopropylamide in 200 ml of dry tetrahydrofuran under a nitrogen atmosphere at $-78°$ C. there are added 0.1 mol of 2-cycloalkyl (or 2-alkenylor 2-cycloalkenyl-)-acetonitrile over a period of 2 minutes and the mixture is stirred for 40 minutes at 0° C. Over a period of 2 minutes 0.1 mol (40.9 g) of triphenylmethylpyridinium-tetrafluoroborate are added in portions at ° C. As soon as all the pyridinium salt has dissolved, the tetrahydrofuran is removed and the residue is taken up in 40 ml of $CHCl_3$. The extract is filtered off and the filtrate is mixed with 30 ml of carbon tetrachloride. The mixture is then stirred overnight. After removal of the solvent, the residue is chromatographed twice (Al$_2$O$_3$, Grade I, neutral; CCl$_4$:CHCl$_3$=1:4; diethylether:CHCl$_3$=1:9).

In DMBA-induced mammary carcinoma[1] of the Sprague—Dawley Rat (postmenopausal model), the compounds according to the present invention display a good inhibition of mammary tumour growth by reduction of the estrogen content to the castration level.

Reduction of the estrogen content was also observed in the PMSG-pretested Sprague-Dawley rat[2].

Using for example the above-mentioned test method with a dose of 0.3 mg/kg body weight in the SD rat (subcutaneous) a 50% reduction in the estradiol level of PMSG-primed rats was achieved.

The lowest effective dose in the above-mentioned animal experiment is, for example, ca. 0.05 mg/kg subcutaneously
1. DMBA=7,12-dimethylbenz[a]-anthracene
2. PMSG=gonadotropin from the serum of pregnant mares
ca. 0.1 mg/kg orally
ca. 0.05 mg/kg intravenously As general active dosage ranges (animal experiment as above) the following may for example be used:

0.1-1.0 mg/kg oral, in particular 0.5
0.05-0.1 mg/kg intravenous
0.1-1.0 mg/kg subcutaneous, in particular 0.5

The general activity of the compounds of the present invention is comparable to the activity of the known medicament aminoglutethimide, but shows in this connection in particular, the following differences: the compounds according to the present invention are active at substantially lower doses; since desmolase inhibition is absent using this dose there is no need to substitute with hydrocortisones; there is no depressive activity on the central nervous system.

Possible indications for the compounds of the present invention include: hormone dependent tumors such as for example mammary carcinoma and endometral carcinoma, endometriosis, gynecomastia idiopathic oligospermia, ovulation inhibitors, benign prostate hyperplasma. The compounds of the present invention may also be used as fertility promoting agents.

The dosage units for the pharmaceutical compositions contain in general between 5 and 50, preferably 10 to 20 mg of the active ingredient(s) according to the present invention. A daily dose which may be used is for example 50 mg of the compound of formula I.

Administration in humans or animals may for example be in the form of tablets, capsules, pills, coated tablets, suppositories, ointments, gels, creams, powder, dusting powder, aerosols or in liquid form. Liquid forms of administration which may be used include, for example, oily or alcoholic or aqueous solutions as well as suspensions and emulsions. Preferred administration forms are tablets, which may contain between 10 and 20 mg, or solutions, which contain between 0.5 and 5 percent by weight of the active substance.

The dosage unit of the active components according to the present invention, especially for human therapy, may for example be (in addition to physiologically acceptable carriers):

(a) in the case of oral medicaments between 5 and 50 mg preferably 10-20 mg
(b) in the case of parental medicaments (for example intravenous, intramuscular) between 1 and 5 ml preferably 2-3 ml (the doses are in each case calculated on the free base form).

1 or 2 tablets may for example be administered 3 times daily, each containing from 5 to 50 mg of the active substance or, for example with an intravenous injection 1 to 3 times daily one ampoule of 1 to 5 ml containing 5 to 50 mg of the active substance. For oral administration, the minimum daily dose may for example be 15 mg of active substance; the maximum daily dose in the case of oral administration should not exceed 300 mg of active substance.

The acute toxicity of the compounds of the present invention in mice (expressed in LD 50 mg/kg; method after Miller and Tainter: Proc. Soc. Exper. Biol. a. Med. 57 (1944) 261) is, for example in the case of oral administration, greater than 600 mg/kg.

The following examples illustrate the invention.

EXAMPLES OF SYNTHESIS OF ACTIVE SUBSTANCES

Example 1

3-(4-aminophenyl)-3-cyclohexyl-piperidine-2,6-dione

A mixture of 0.1 mol of 2-cyclohexyl-2-phenyl-glutaric acid dinitrile, 160 ml concentrated H$_2$SO$_4$ and 500 ml of glacial acetic acid was heated for 6 hours over a water bath. After cooling, the mixture was poured onto ice and shaken with CH$_2$Cl$_2$. The organic phase was washed with saturated Na$_2$CO$_3$ solution and then with H$_2$O. The solvent was removed and the 3-cyclohexyl-3-phenylpiperidine-2,6-dione was recrystallized from ethyl acetate/ligroin. Yield 75% of theory.

To a solution of 3-cyclohexyl-3-phenyl-piperidine-2,6-dione (0.05 mol) in 40 g concentrated H$_2$SO4 At −10° C. a mixture of 5.5 g concentrated H$_2$SO$_4$ and 5.5 g of 70% HNO$_3$ was added dropwise.

The reaction mixture was held for 2 hours at −10° C. The reaction product was then poured onto ice and extracted with CH$_2$Cl$_2$. The organic phase was washed with saturated Na$_2$CO$_3$ solution and then washed wth H$_2$O and dried over Na$_2$SO$_4$. After removal of the solvent the so-obtained 3-cyclcohexyl-3(4-nitrophenyl)-piperidine-2,6-dione was recrystallized from toluene. M.P. 155-7° C. (Yield 97% of theory).

A solution of 3-cycloalkyl-3-(4-nitrophenyl)-piperidine-2,6-dione (0.01 mol), in 100 ml of ethanol, was treated wtih palladium on active charcoal (10%, 0.1g). The mixture was shaken under a hydrogen atmosphere until there was no further hydrogen uptake. The suspension was purified by recrystalization from toluene. M.P. 189°-190° C. Yield 73% of theory.

Preparation of the starting materials
2-Cyclohexyl-2-pheny-acetonitrile

To a solution of benzylcyanide (58.5 g, 0.5 mol) and cyclohexylbromide (0.5 mol) in 200 ml of dry benzene there was added, at 80° C., 0.5 mol of sodium amide.

The reaction mixture was heated for 2 hours. After cooling, 200 ml of H$_2$O were added, the organic phase was separated, washed with H$_2$O and dried over Na$_2$SO$_4$. After removal of the solvent the product was recrystallized from diethylether. (Yield 50% of theory).

2-cyclohexyl-2-phenyl-glutaric acid dinitrile

To a mixture of 0.3 mol of 2-cyclohexyl-2-phenylacetonitrile, 0.3 mol of a non-ionic alkylarylpolyether alcohol or an alkylphenylether of polyethylene glycol (Triton B) and 300 ml of dry dioxane, there was added, at a temperature of 100° C., 15.9 g, (0.3 mol) of acrylonitrile and the mixture was heated for 40 hours under reflux. After removal of the solvent the residue was extracted with CHCl₃. The chloroform phase was washed with H₂O and dried over Na₂SO₄. The solvent was removed and the oily crude product was purified by column chromatography under nitrogen. (Silica gel, CH₂Cl₂: petroleum ether =4:1) (Yield 55% of theory).

Example 2

3-(4-aminophenyl)-3-cyclopentyl-piperidine-2,6-dione

The compound was prepared in a manner analogous to that described in Example 1 except that the starting material was 0.1 mol of 2-cyclopentyl-2-phenyl-glutaric acid dinitrile. M.P. 138°–140° C. (Yield 73% of theory).

EXAMPLES FOR PHARMACEUTICAL FORMULATIONS

Tablets containing 250 mg of active ingredient 750 g of active ingredient according to Example 1, 225 g of lactose, 94 g of cornstarch and 3 g of aerosil were mixed in a suitable vortex granulating apparatus and sprayed with 120 g of a 10% gelatin solution for granulation purposes. The dry granulate, 78 g of cornstarch, 30 g of talc and 6 g of magnesium stearate were passed through a sieve of 0.8 mm mesh size and homogenized. The mass was pressed in a conventional manner in a suitable machine to scored tablets each weighing 400 mg and having a diameter of .11 mm. Each tablet contained 250 mg of active ingredient.

Example 4

Capsules containing 250 mg of active ingredient 750 mg of active ingredient according to Example 2, 90 g of lactose, 183 g of microcrystalline cellulose, 3 g of aerosil, 21 g of talc and 3 g of magnesium stearate were passed through a sieve (0.8 mm mesh size) and this mixture was homogenized in a suitable apparatus. This mass was filled in a suitable capsule filling machine into No. 1 size hard gelatin capsules each containing 350 mg. Each capsule contained 250 mg active ingredient.

It will be appreciated that various changes may be made in details of composition and mode of synthesis described in the foregoing examples without departing from the scope of the present invention as described in the following claims.

What is claimed is:

1. 3-aryl-3-cycloalkyl-piperidine-2,6-dione derivatives useful for inhibiting estrogen biosynthesis of the general formula I:

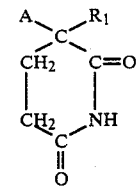

in which A is a 4-aminophenyl radical and $R_1$ is a saturated $C_3$-$C_{10}$-cycloalkyl radical as well as physiologically acceptable salts thereof.

2. 3-aryl-3-cycloalkyl-piperidine-2,6-dione derivatives as set forth in claim 1 in which $R_1$ is a $C_4$–$C_8$-cycloalkyl radical.

3. 3-aryl-3-cycloalkyl-piperidine-2,6-dione derivatives as set forth in claim 2 in which $R_1$ is selected from the group consisting of cyclobutyl, cyclopentyl, cyclohexyl, cycloheptyl and cyclooctyl radicals.

4. 3-(4-aminophenyl)-3-cyclohexyl-piperidine-2,6-dione and physiologically acceptable salts thereof.

5. 3-(4-aminophenyl)-3-cyclopentyl-piperidine-2,6-dione and physiologically acceptable salts thereof.

6. A pharmaceutical composition comprising the novel 3-aryl-3-cycloalkyl-piperidine-2,6-dione derivative of claim 1, together with a physiologically acceptable carrier therefor.

7. A method for the treatment of an estrogen dependent disease which comprises administering to a subject in need thereof an effective amount of the compound of claim 1.

* * * * *